United States Patent [19]

Sato et al.

[11] Patent Number: 5,616,786

[45] Date of Patent: Apr. 1, 1997

[54] METHOD OF OBTAINING ANHYDROUS PHENYLALANINE CRYSTALS

[75] Inventors: Takeru Sato; Chiaki Sano, both of Kawasaki, Japan

[73] Assignee: Ajinomoto Co., Inc., Tokyo, Japan

[21] Appl. No.: 533,943

[22] Filed: Sep. 26, 1995

[30] Foreign Application Priority Data

Sep. 26, 1994 [JP] Japan .................................. 6-229255

[51] Int. Cl.$^6$ ................................................ C07C 229/28
[52] U.S. Cl. .......................................... 562/401; 562/443
[58] Field of Search ................................. 562/445, 401, 562/443

[56] References Cited

U.S. PATENT DOCUMENTS 4,399,304  8/1983  Matsuishi et al. ..................... 562/445

Primary Examiner—Samuel Barts
Assistant Examiner—Joseph M. Conrad, III
Attorney, Agent, or Firm—Oblon, Spivak, McClelland, Maier & Neustadt, P.C.

[57] ABSTRACT

A method of obtaining optically active anhydrous phenylalanine crystals from an aqueous solution containing optically active phenylalanine, which involves crystallizing and precipitating optically active phenylalanine from an optically active phenylalanine super-saturated solution at a temperature, T, wherein the super-saturated solution is required to have an osmotic pressure $\pi$ (mOsm/kg.$H_2O$) which is related to said temperature T in accordance with the following formula (I):

$$\pi \geq 10{,}500 - 450T + 4.4T^2 \qquad (I),$$

wherein the method provides anhydrous crystals having excellent handleability.

4 Claims, 1 Drawing Sheet

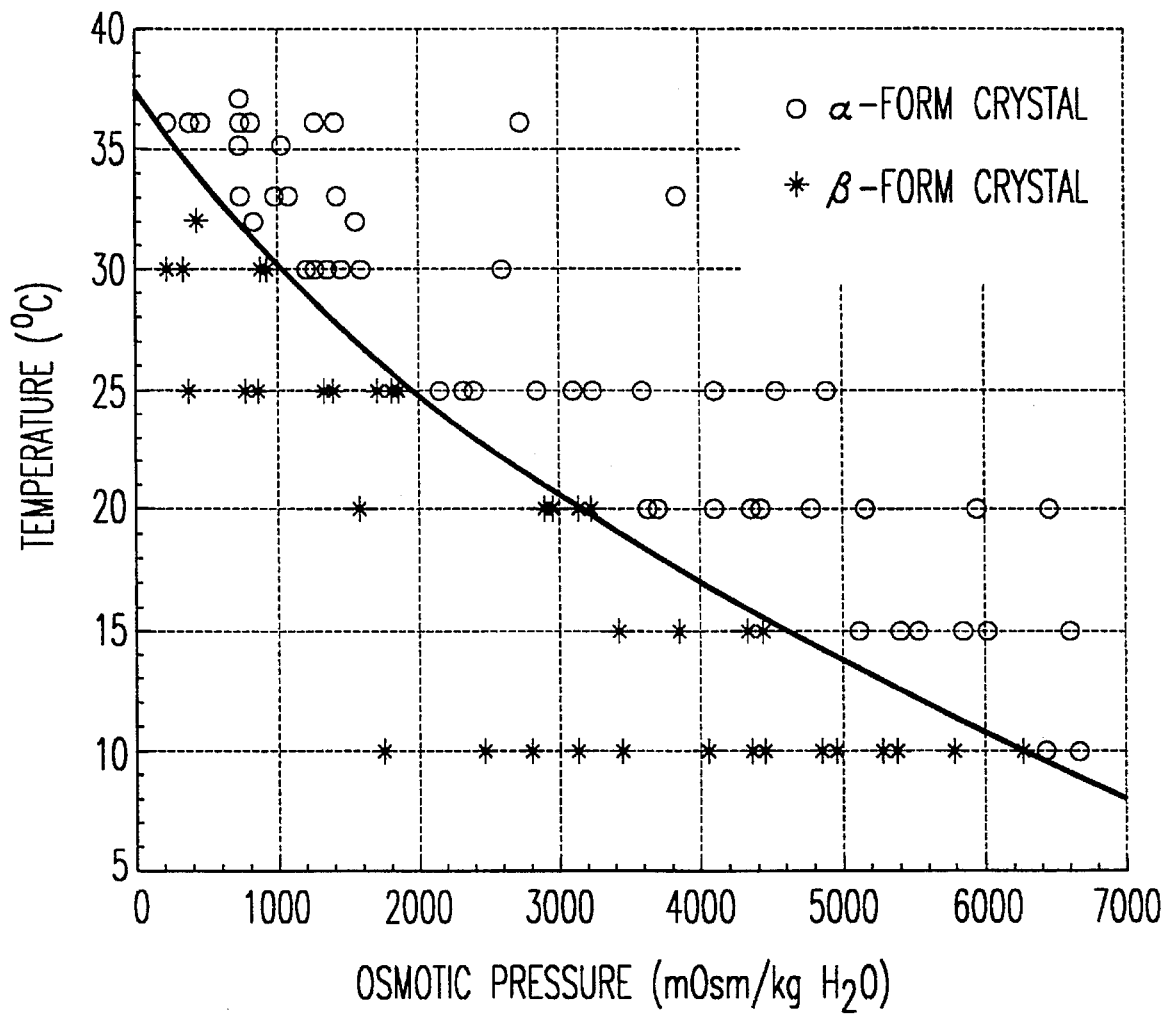

METHOD OF OBTAINING ANHYDROUS PHENYLALANINE CRYSTALS

BACKGROUND OF THE INVENTION

1. Field of the Invention

The present invention relates to a method for obtaining optically active anhydrous phenylalanine crystals which are useful as a pharmaceutical starting powder, a pharmaceutical intermediate and a starting material of a sweetener.

2. Prior Art

L-phenylalanine is an essential amino acid which is nutritionally indispensable, and is industrially useful as a starting material in the preparation of L-aspartyl-L-phenylalanine methyl ester, which is a sweetener.

Optionally active phenylalanine is conventionally obtained by (a) separation from a hydrolyzate of a protein such as defatted soybean, (b) by fermentation or (c) by direct synthesis. In these methods, crystallization and precipitation of the optically active phenylalanine are generally carried out to purify it. When the optically active phenylalanine-containing solution is crystallized and precipitated at a pH in the range of from 3 to 9, either anhydrous crystals (hereafter referred to as "α-form crystals") or monohydrate crystals (hereafter referred to as "β-form crystals") of the optically active phenylalanine are obtained. The α-form crystals are plate or flake crystals, while the β-form crystals are fine needle crystals. Further, the α-form crystals exhibit good separability from the mother liquor, and show less entrainment of the mother liquor. Therefore, α-form crystals are industrially preferred over β-form crystals. Thus, methods of obtaining high-quality α-form crystals stably have been extensively studied.

The following methods have been previously used to obtain high-quality α-form crystals:

(1) Japanese Laid Open Patent Application (Kokai) No. 91,062/1992 discloses a method in which sodium chloride in an amount of at least 20 g/100 g.H$_2$O is added to a phenylalanine-containing aqueous solution, and the mixture is cooled to 30° C. or lower to crystallize and precipitate phenylalanine.

(2) Japanese Laid-Open Patent Application (Kokai) No. 103,565/1992 discloses a method in which a surfactant such as a sorbitan alkyl ester or polyoxyethylenesorbitan alkyl ester is added to an aqueous solution containing phenylalanine and ammonium chloride to crystallize and precipitate phenylalanine.

(3) Japanese Laid-Open Patent Application (Kokai) No. 304,971/1993 discloses a method in which, when the concentration of phenylalanine in the phenylalanine fermentation liquid is above the solubility during cultivation, α-form seed crystals are added to crystallize and precipitate phenylalanine.

Further, the following methods have been previously used to obtain phenylalanine in high yield:

(4) Japanese Laid Open Patent Application (Kokai) No. 163,215/1993 discloses a method of isolating phenylalanine in which from 20 to 40% by weight of ammonium sulfate are added to a phenylalanine-containing aqueous solution, and the mixture is filtered at a temperature of 30° C. or lower.

(5) Japanese Laid-Open Patent Application (Kokai) No. 178,801/1993 discloses a method of crystallizing and precipitating phenylalanine in which at least 8% by weight of ammonium sulfate are added to a phenylalanine aqueous solution obtained by an enzymatic reaction of cinnamic acid and ammonia.

However, these methods have not been studied for obtaining the α-form crystals stably. Even if the α-form crystals are formed, only the concentration of each additive in the crystallizing solution has been defined. Systematic considerations have not been offered.

SUMMARY OF THE INVENTION

Accordingly, one object of the present invention is to provide a method in which high quality phenylalanine crystals are obtained while maintaining excellent handleability in the step of crystallizing and precipitating L-phenylalanine.

A further object of the present invention is to provide a method for providing high-quality α-form crystals which minimizes the amount of added inorganic salt, such as sodium chloride and ammonium sulfate, needed during precipitation and crystallization.

These and other objects of the present invention have been satisfied by the discovery of a method of obtaining optically active anhydrous phenylalanine crystals from an aqueous solution containing optically active phenylalanine, which comprises crystallizing and precipitating optically active phenylalanine from an optically active phenylalanine super-saturated solution at a temperature, T, wherein the super-saturated solution is required to have an osmotic pressure πO (mOsm/kg.H$_2$O) which is related to said temperature T in accordance with the following formula (I):

$$\pi \geq 10{,}500 - 450T + 4.4T^2 \qquad (I).$$

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a graphical representation showing the crystal form of precipitated optically active phenylalanine wherein the crystallization/precipitation temperature is plotted as the ordinate and the osmotic pressure of the solution as the abscissa respectively.

DETAILED DESCRIPTION OF THE PREFERRED EMBODIMENTS

The present invention relates to a method of obtaining optically active anhydrous phenylalanine crystals from an aqueous solution containing optically active phenylalanine, which comprises crystallizing and precipitating optically active phenylalanine from an optically active phenylalanine super-saturated solution at a temperature, T, wherein the super-saturated solution is required to have an osmotic pressure π (mOsm/kg.H$_2$O) which is related to said temperature T in accordance with the following formula (I):

$$\pi \geq 10{,}500 - 450T + 4.4T^2 \qquad (I).$$

Optically active phenylalanine is formed as α-form crystals at a given temperature (transition point) and as β-form crystals at a temperature below that given temperature. In an aqueous system, the transition point of optically active phenylalanine is approximately 37° C. The obtained crystals can be estimated as α-form crystals or as β-form crystals through observation using such means as a microscope or powder X-ray analysis. However, the transition point has been generally difficult to measure. The reason is that even if phenylalanine is crystallized and precipitated at a temperature of 40° C., which is deemed to be within an α-crystal region, β-form crystals are precipitated when the concentration of the optically active phenylalanine in the solution becomes high and the transition point is apparently estimated to increase.

Careful observation of the crystallization/precipitation temperature, the concentration of the optically active phenylalanine in the solution, the osmotic pressure of the solution and the crystal form of the optically active phenylalanine precipitated has provided the present process for precipitating optically active anhydrous phenylalanine crystals. FIG. 1 shows that the α-form crystals are formed at a high osmotic pressure of the solution, and the β-form crystals are formed at a low osmotic pressure of the solution. The borderline between the α-crystal region and the β-crystal region is expressed in terms of the crystallization/precipitation temperature and the osmotic pressure of the solution. In accordance with the present process, to obtain α-form crystals at a given crystallization/precipitation temperature T (°C.), the optically active phenylalanine-containing solution is crystallized and precipitated upon adjusting the osmotic pressure ($\pi$) of the solution to at least 10,500–450T +4.4 $T^2$. This makes it possible to obtain the α-form crystals stably even if the crystallization/precipitation temperature T (°C.) is below the transition point in a pure system. Thus, even when phenylalanine is crystallized and precipitated in an aqueous system at a temperature below 37° C., which is the transition point of the aqueous system, the α-form crystals, which were difficult to obtain previously, can be formed stably and easily upon adjusting the osmotic pressure as mentioned above.

The osmotic pressure here referred to is a value measured by means of an osmometer based on freezing point depression, and the unit is mOsm/kg.$H_2O$.

An osmotic pressure increasing additive can be used to adjust the osmotic pressure $\pi$ of the optically active phenylalanine-containing solution to a desired value. Any additive can be used so long as it helps to give a desired osmotic pressure at the desired crystallization/precipitation temperature. The osmotic pressure increasing additives include inorganic and organic compounds. Examples of the inorganic compounds include electrolytes, including chlorides such as aluminum chloride, ammonium chloride, potassium chloride and sodium chloride, nitrates such as ammonium nitrate, potassium nitrate and sodium nitrate, carbonates such as ammonium carbonate, and sulfates such as aluminum sulfate, ammonium sulfate, aluminum potassium sulfate, sodium sulfate and magnesium sulfate. Examples of the organic compounds include organic electrolytes such as sodium acetate, potassium acetate, sodium oxalate and potassium oxalate, and non-electrolytes, including saccharides such as galactose, glucose, fructose, mannose, sucrose, lactose and maltose, and high-molecular weight substances such as polyethylene glycol. Also available are monohydric alcohols such as methanol and ethanol, and polyhydric alcohols such as ethylene glycol and glycerol. These compounds may be used either singly or in combination so long as the desired osmotic pressure can be provided. The low molecular weight electrolytes such as the inorganic salts are preferable in view of the increase in the osmotic pressure.

Some additives, such as sodium chloride, decrease the solubility of the optically active phenylalanine. In that case, the concentration (g/100 g.$H_2O$: hereinafter referred to as "C1") of the optically active phenylalanine before the crystallization and precipitation is unchanged, but the concentration (hereinafter referred to as "C2") of the optically active phenylalanine in the mother liquor after the optically active phenylalanine has been crystallized and precipitated with the additive decreases, with the result that the degree of supersaturation (C1/C2) at the time of crystallization and precipitation increases. When the degree of supersaturation C1/C2 at the time of crystallization and precipitation exceeds 3, the β-form crystals are temporarily precipitated. Accordingly, it has to be considered that when the additive is added, the osmotic pressure is raised and the degree of supersaturation therefore increases. Consequently, it is preferred to conduct the crystallization and precipitation at C1/C2 within the range of from 1 to 3, and preferably from 1 to 2. Thus, when using additives which decrease the solubility of optically active phenylalanine, such as sodium chloride, it is preferred to add no more than 10% excess above that amount which is needed to adjust the osmotic pressure to satisfy Formula (I).

The optically active phenylalanine-containing aqueous solution for use in the crystallization and precipitation process of the present invention can be any phenylalanine containing solution so long as the optically active phenylalanine can be crystallized and precipitated therefrom. Suitable solutions include a fermentation liquid, a solution obtained by treating the fermentation liquid with an ion-exchange resin or a decoloring agent, a solution of crude crystals obtained by crystallizing and precipitating the above-mentioned solution, and a mother liquor from which the crude crystals have been separated in the fermentation method; a protein hydrolyzate, a solution obtained by treating the protein hydrolyzate with an ion-exchange resin or a decoloring resin, a solution of crude crystals obtained by crystallizing and precipitating the above-mentioned solution, and a mother liquor from which the crude crystals have been separated in the protein hydrolysis method; and a solution obtained by reacting DL-acetylphenylalanine with an acylase. For example, optically active phenylalanine can be effectively crystallized and precipitated from the optically active phenylalanine-containing aqueous solution having high osmotic pressure, such as the fermentation liquid, because the additive for adjusting the osmotic pressure to a desired value may be used in a small amount.

Having generally described this invention, a further understanding can be obtained by reference to certain specific examples which are provided herein for purposes of illustration only and are not intended to be limiting unless otherwise specified.

EXAMPLES

In the following Examples, C1 refers to the concentration (g/100 g.$H_2O$) of optically active phenylalanine before crystallization and precipitation, and C2 refers to the concentration (g/100 g.$H_2O$) of optically active phenylalanine in the mother liquor after crystallization and precipitation.

Example 1

Fifty grams of water were added to 1.7 g of L-phenylalanine crystals (made by Sigma Co.), and the L-phenylalanine crystals were dissolved therein at 60° C. to prepare a L-phenylalanine solution having a L-phenylalanine concentration C1 of 3.4. Ammonium sulfate was then added to the solution to provide a predetermined osmotic pressure, and was dissolved therein at 60° C. The mixture was then cooled to 30° C. to crystallize and precipitate L-phenylalanine. At that time, ammonium sulfate was added in amounts of 2.5 g, 5 g, 6 g and 8 g such that the predetermined-osmotic pressure became higher than 960 (=10,500−450×30+4.4×30×30) (mOsm/kg.H$_2$O). By comparison, ammonium sulfate was added in amounts of 0 g, 1 g and 2 g such that the osmotic pressure became lower than 960 (mOsm/kg.H$_2$O), and the resulting mixtures were also crystallized and precipitated. The phenylalanine concentration in the mother liquor and the crystal form of the obtained phenylalanine are shown in Table 1.

As shown in Table 1, anhydrous crystals (α-form crystals) were obtained preferentially when the osmotic pressure was higher than 960 (mOsm/kg.H$_2$O).

TABLE 1

| | Amount of ammonium sulfate (g) | Osmotic pressure π (mOsm/kg .H$_2$O) | Form of crystal precipitated | Phenylalanine concentration C2(g/100 g.H$_2$O) | C1/C2 |
|---|---|---|---|---|---|
| Comparative Examples | 0 | 160 | β-form | 3.1 | 1.1 |
| | 1 | 516 | β-form | 3.0 | 1.1 |
| | 2 | 784 | β-form | 2.9 | 1.2 |
| Examples | 2.5 | 964 | α-form | 2.6 | 1.3 |
| | 5 | 1621 | α-form | 2.4 | 1.4 |
| | 6 | 1861 | α-form | 2.2 | 1.5 |
| | 8 | 2350 | α-form | 2.0 | 1.7 |

Examples 2

Fifty grams of H$_2$O were added to 1.8 g of L-phenylalanine crystals (made by Sigma Co.), and the L-phenylalanine crystals were dissolved therein at 60° C. to prepare a L-phenylalanine solution having a L-phenylalanine concentration C1 of 3.6. Dextrose was then added to the solution to provide a predetermined osmotic pressure, and was dissolved therein at 60° C. The mixture was then cooled to 25° C. to crystallize and precipitate L-phenylalanine. At that time, dextrose was added in amounts of 20 g, 25 g and 30 g such that the predetermined osmotic pressure became higher than 2,000 (=10,500−450×25 +4.4×25×25) (mOsm/kg.H$_2$O). By comparison, dextrose was added in amounts of 8 g, 12 g and 16 g such that the osmotic pressure became lower than 2,000 (mOsm/kg.H$_2$O) and the resulting mixtures were also crystallized and precipitated. The phenylalanine concentration in the mother liquor and the crystal form of the obtained phenylalanine are shown in Table 2.

As shown in Table 2, anhydrous crystals (α-form crystals) were obtained preferentially when the osmotic pressure was higher than 2,000 (mOsm/kg.H$_2$O).

TABLE 2

| | Amount of dextrose (g) | Osmotic pressure π (mOsm/kg .H$_2$O) | Form of crystal precipitated | Phenylalanine concentration C2(g/100 g.H$_2$O) | C1/C2 |
|---|---|---|---|---|---|
| Comparative Examples | 8 | 1100 | β-form | 2.9 | 1.2 |
| | 12 | 1623 | β-form | 3.0 | 1.2 |
| | 16 | 1816 | β-form | 3.1 | 1.2 |
| Examples | 20 | 2182 | α-form | 3.3 | 1.1 |
| | 25 | 2716 | α-form | 3.4 | 1.1 |
| | 30 | 3130 | α-form | 3.5 | 1.03 |

Example 3

Fifty grams of water were added to 1.7 g of L-phenylalanine crystals (made by Sigma Co.), and the L-phenylalanine crystals were dissolved therein at 60° C. to prepare a solution having the L-phenylalanine concentration C1 of 3.4. Sodium chloride was then added to the solution in amounts of 6 g, 8 g, 10 g and 12 g, and was dissolved therein at 60° C. to prepare four phenylalanine aqueous solutions. Subsequently, these solutions were cooled to a predetermined temperature to crystallize and precipitate L-phenylalanine. The conditions of the experiment and the results (crystal form of phenylalanine) are shown in Table 3. The osmotic pressures of the solutions which were borderlines between α-form crystals and β-form crystals at the crystallization/precipitation temperatures (25° C., 20° C., 15° C. and 10° C.) were 2,000, 3,260, 4,740 and 6,440 (mOsm/kg.H$_2$O) respectively.

Table 3 reveals that the anhydrous crystals (α-form crystals) were obtained preferentially when the osmotic pressures of the phenylalanine aqueous solutions were higher than those of the solutions which were borderlines between α-form crystals and β-form crystals at the crystallization/precipitation temperatures.

TABLE 3

| Amount of NaCl (g) | Upper line: Middle Line: Lower Line: | Osmotic pressure π (mOsm/kg.H$_2$O) of the solution<br>Form of crystal precipitated<br>Phenylalanine concentration C2 (g/100 g.H$_2$O) | | |
|---|---|---|---|---|
| | | 25° C. | 20° C. | 15° C. | 10° C. |
| 6 | | 3642<br>α-form<br>2.1<br>(C1/C2 = 1.6) | 3666<br>α-form<br>2.0<br>(C1/C2 = 1.7) | 3728<br>β-form<br>1.9<br>(C1/C2 = 1.8) | 3710<br>β-form<br>1.9<br>(C1/C2 = 1.8) |
| 8 | | 4918<br>α-form<br>1.8<br>(C1/C2 = 1.9) | 4836<br>α-form<br>1.7<br>(C1/C2 = 2.0) | 4844<br>α-form<br>1.7<br>(C1/C2 = 2.0) | 4855<br>β-form<br>1.6<br>(C1/C2 = 2.1) |
| 10 | | 5995<br>α-form<br>1.6<br>(C1/C2 = 2.1) | 5960<br>α-form<br>1.5<br>(C1/C2 = 2.3) | 6036<br>α-form<br>1.4<br>(C1/C2 = 2.4) | 5872<br>β-form<br>1.4<br>(C1/C2 = 2.4) |
| 12 | | 7075<br>α-form<br>1.4<br>(C1/C2 = 2.4) | 7092<br>α-form<br>1.3<br>(C1/C2 = 2.6) | 7055<br>α-form<br>1.2<br>(C1/C2 = 2.8) | 7020<br>α-form<br>1.2<br>(C1/C2 = 2.8) |

Example 4

L-phenylalanine crystals (made by Sigma Co.) were dissolved at 70° C., and four kinds of L-phenylalanine solutions having the L-phenylalanine concentrations C1 of 5.2, 4.5, 3.5 and 3.0 were prepared. Then, 9 g of sodium chloride were added to each of the solutions, and dissolved therein at 70° C. The mixture was cooled to 15° C. to crystallize and precipitate L-phenylalanine. The phenylalanine concentration in the mother liquor and the crystal form of phenylalanine are shown in Table 4. The osmotic pressure of the solution was a borderline between α-form crystals and β-form crystals at the crystallization/precipitation temperature of 15° C. and was 4,740 (=10,500−450×25+4.4×25×25) (mOsm/kg.H$_2$O) As shown in Table 4, even if the osmotic pressure was higher than 4,740 (mOsm/kg.H$_2$O), the β-form crystals were precipitated in the system with C1/C2 of 3.1 in combination with the α-form crystals. Meanwhile, only the α-form crystals were precipitated in the system with C1/C2 of less than 3.

TABLE 4

| Phenylalanine concentration (g/100 g.H$_2$O) | Osmotic pressure π (mOsm/kg.H$_2$O) | Form of crystal precipitated | Phenylalanine concentration C2 (g/100 g.H$_2$O) | C1/C2 |
|---|---|---|---|---|
| 5.2 | 5370 | α-form + β-form | 1.7 | 3.1 |
| 4.5 | 5424 | α-form | 1.7 | 2.6 |
| 3.5 | 5484 | α-form | 1.7 | 2.1 |
| 3.0 | 5292 | α-form | 1.7 | 1.8 |

Example 5

A L-phenylalanine fermentation liquid produced according to Example 1 of Japanese Patent second publication (Kokoku) No. 21,079/1976 was centrifuged and sterilized. The sterile liquid was concentrated, then cooled, crystallized and precipitated. The crystals precipitated were separated, washed, and dried to obtain L-phenylalanine crude crystals having a L-phenylalanine content of 95%. The crude crystals (1.7 g) were dissolved in 50 g of water at 60° C. to obtain a solution having a L-phenylalanine concentration C1 of 3.2. Subsequently, 25 g of dextrose were added to the solution, and dissolved therein at 60° C. NaCl was added to the mixture such that a predetermined osmotic pressure was reached, and was dissolved therein at 60° C. The mixed solution was cooled to 15° C. to crystallize and precipitate L-phenylalanine. At that time, NaCl was added in amounts of 5 g, 6 g and 7 g such that the predetermined osmotic pressure became higher than 4,740 (=10,500−450×15+4.4×15×15) (Osm/kg.H$_2$O) By comparison, NaCl was added in amounts of 2 g, 3 g and 4 g such that the osmotic pressure became lower than 4,740 mOsm/kg.H$_2$O, and the resulting mixtures were also crystallized and precipitated. The phenylalanine concentration in the mother liquor and the crystal form of the obtained phenylalanine are shown in Table 5.

Table 5 shows that the anhydrous crystals (α-form crystals) were obtained preferentially when the osmotic pressure was higher than 4,740 (mOsm/kg.H$_2$O)

TABLE 5

| | Amount of dextrose (g) | Amount of NaCl (g) | Osmotic pressure π (mOsm/kg.H$_2$O) | Form of crystal precipitated | C2 (g/100 g.H$_2$O) | C1/C2 |
|---|---|---|---|---|---|---|
| Comparative Examples | 25 | 2 | 3456 | β-form | 2.9 | 1.1 |
| | 25 | 3 | 3916 | β-form | 2.7 | 1.2 |
| | 25 | 4 | 4444 | β-form | 2.5 | 1.3 |
| Examples | 25 | 5 | 4872 | α-form | 2.4 | 1.3 |
| | 25 | 6 | 5364 | α-form | 2.3 | 1.4 |
| | 25 | 7 | 5864 | α-form | 2.2 | 1.5 |

Example 6

The L-phenylalanine fermentation liquid obtained in Example 5 was concentrated to obtain a solution having a L-phenylalanine concentration C1 of 4.0 (g/100 g.H$_2$O). Then, ammonium sulfate was added to the solution such that the solution was adjusted to a predetermined osmotic pressure, and was then dissolved therein at 40° C. The mixed solution was cooled to 20° C to crystallize and precipitate L-phenylalanine. At that time, ammonium sulfate was added in amounts of 8 g, 10 g and 12 g such that the predetermined osmotic pressure became higher than 3,260 (=10,500−450× 20+4.4×20×20) (mOsm/kg.H$_2$O). By comparison, ammonium sulfate was added in amounts of 2 g, 4 g and 6 g such that the osmotic pressure became lower than 3,260 (mOsm/ kg.H$_2$O), and the resulting mixtures were also crystallized and precipitated. The phenylalanine concentration in the mother liquor and the crystal form of the obtained phenylalanine are shown in Table 6.

Table 6 shows that the anhydrous crystals (α-form crystals) were obtained preferentially when the osmotic pressure was higher than 3,260 (mOsm/kg.H$_2$O).

TABLE 6

| | Amount of ammonium sulfate (g) | Osmotic pressure π (mOsm/kg.H$_2$O) | Form of crystal precipitated | Phenylalanine concentration C2 (g/100 g.H$_2$O) | C1/C2 |
|---|---|---|---|---|---|
| Comparative Examples | 2 | 1992 | β-form | 2.7 | 1.5 |
| | 4 | 2567 | β-form | 2.6 | 1.5 |
| | 6 | 2890 | β-form | 2.4 | 1.7 |
| Examples | 8 | 3450 | α-form | 2.2 | 1.8 |
| | 10 | 3966 | α-form | 2.0 | 2.0 |
| | 12 | 4376 | α-form | 1.8 | 2.2 |

As shown above, according to the present invention, optically active anhydrous phenylalanine crystals having excellent separability can be stably obtained. With improved yield making the process advantageous for use in industrial production.

This application is based on Japanese Patent Application 229255/1994, filed with the Japanese Patent Office on Sep. 26, 1994, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method of obtaining α-form crystals of anhydrous phenylalanine from an aqueous solution, which comprises the steps of:

adding one or more osmotic pressure increasing additives to said aqueous solution such that the osmotic pressure (π, mOsm/kg.H$_2$O) of said aqueous solution is $$\pi \geq 10,500 - 450T° 4.4T^2$$

where T is the temperature of crystallization of the aqueous solution; and crystallizing said α-form crystals of anhydrous phenylalanine.

2. The method of claim 1, wherein T is not higher than 37° C.

3. The method of claim 1, wherein said aqueous solution has a phenylalanine concentration, C1, and, after said crystallization, a mother liquor is obtained having a phenylalanine concentration, C2, wherein C1/C2 is in a range of from 1 to 3.

4. The method of claim 1, wherein said one or more osmotic pressure increasing additives is a member selected from the group consisting of aluminum chloride, ammonium chloride, potassium chloride, sodium chloride, ammonium nitrate, potassium nitrate, sodium nitrate, ammonium carbonate, aluminum sulfate, ammonium sulfate, potassium sulfate, aluminum sulfate, sodium sulfate, magnesium sulfate, sodium acetate, potassium acetate, sodium oxalate, potassium oxalate, galactose, glucose, fructose, mannose, sucrose, lactose, maltose, methanol, ethanol, propanol, and mixtures thereof.

* * * * *